(12) United States Patent
Walker

(10) Patent No.: US 6,413,909 B1
(45) Date of Patent: Jul. 2, 2002

(54) HERBICIDE COMPOSITION FOR CONTROL OF RYE GRASS AND VETCH IN PREPLANT BURNDOWN

(76) Inventor: Larry L. Walker, 145A Shady Grove Rd., Flintville, TN (US) 37335

( * ) Notice: Subject to any disclaimer, the term of this patent is extended or adjusted under 35 U.S.C. 154(b) by 0 days.

(21) Appl. No.: 09/885,148

(22) Filed: Jun. 20, 2001

(51) Int. Cl.⁷ ............................................... A01N 43/64
(52) U.S. Cl. ..................................................... 504/134
(58) Field of Search ......................................... 504/134

(56) References Cited

U.S. PATENT DOCUMENTS

| | | |
|---|---|---|
| 4,824,475 A | 4/1989 | Markley et al. |
| 4,838,928 A | 6/1989 | Arenstein et al. |
| 5,763,359 A | 6/1998 | Costales et al. |
| 5,968,873 A | 10/1999 | Dahmen et al. |
| 5,994,269 A | 11/1999 | Bugg et al. |

FOREIGN PATENT DOCUMENTS

| WO | 9854967 | * 12/1998 |
|---|---|---|

* cited by examiner

Primary Examiner—Alton Pryor
(74) Attorney, Agent, or Firm—Lanier Ford Shaver & Payne P.C.; Gerald M. Walsh

(57) ABSTRACT

A herbicide composition for burndown treatment comprising ametryn, atrazine, and paraquat wherein the amounts of atrazine and paraquat are substantially reduced compared to amounts required when used without ametryn.

19 Claims, No Drawings

HERBICIDE COMPOSITION FOR CONTROL OF RYE GRASS AND VETCH IN PREPLANT BURNDOWN

BACKGROUND OF THE INVENTION

1. Field of the Invention

The present invention relates to herbicides and, more particularly, to herbicides for the control of preplant burndown.

2. Background of the Invention

Providing a newly planted crop an even start with weeds has been a major objective of modern weed management systems. Whether in conventional tillage or no-till there is a need to plant the crop in a weed-free seed bed. Weeds present at planting will grow much quicker than the crop and, thus, become competitive very early in the growing season. A complete removal of weeds from the soil with herbicides before planting is referred to as a "burndown."

Performing a herbicide burndown one to three weeks before planting a crop, such as corn, allows vegetation to decompose and allows for retreatment if necessary. Using triazines, such as atrazine, for burndown is useful in removing broadleafs but is not adequate for many grasses, such as rye grass. Gramoxone (paraquet) is about 75–80% effective against rye grass and has some effectiveness against broadleafs. The combination of atrazine and paraquat is 85–95% effective against broadleafs and grasses, including rye grass, but is not as effective on vetch. Vetch is a winter annual legume and must also be controlled in burndown. Atrazine is 65–75% effective against vetch and paraquet is also 65–75% effective against vetch. Atrazine plus paraquat is 75–85% effective against vetch. In order to achieve this level of effectiveness on rye grass and vetch, atrazine must be administered at 1.6 to 2.0 lbs. active ingredient per acre and paraquat at 0.5 to 1.0 lbs. active ingredient per acre.

Ametryn gives control of both broadleafs and grasses. Ametryn is also known to be 100% effective against vetch. Nevertheless, Ametryn alone or in mixtures is not recommended for burndown and is not known to be useful in burndown.

Atrazine and paraquet are restricted-use herbicides. Atrazine is restricted because of its potential for ground water and drinking water contamination. Paraquat is restricted because of its high toxicity to humans and other mammals, having an EPA toxicity class I rating. Ametryn, on the other hand, is unrestricted because it has minimal human toxicity and much less potential to contaminate ground water or drinking water, compared to atrazine.

I have discovered that ametryn in combination with reduced amounts of atrazine and paraquat is a superior composition for use in burndown, and is less toxic and less contaminating than the combination of atrazine and paraquat presently in use.

SUMMARY OF THE INVENTION

The present invention is a composition of ametryn, atrazine, and paraquat as active ingredients in the proportions of ametryn 1.14 to 1.52 lbs. to atrazine 0.25 to 1.0 lbs. to paraquat 0.25 to 0.5 lbs. The percentage of each herbicide by weight in the composition is, thus, ametryn about 50–60%, atrazine about 20–35%, and paraquat about 17–23%. 1.0 to 3.5 lbs. of this composition is suspended in 20 gallons of water plus 0.5% v/v surfactant or 1 pint of crop oil concentrate, to apply per acre. This composition is applied 5 to 21 days before planting. Field tests show that this composition of the present invention will produce a 92–100% burndown, including rye grass and vetch. Because of significant reduced amounts of atrazine and paraquat in the present composition, there is significantly less human toxic exposure and ground water and drinking water contamination with this composition, compared to the standard use of atrazine combined only with paraquat for burndown. An advantage of the present invention is a preplant burndown herbicide composition which provides less human toxic exposure and less ground water and drinking water contamination.

Another advantage of the present invention is a preplant burndown herbicide composition which produces 92–100% burndown, including rye grass and vetch.

Another advantage of the present invention is a preplant burndown herbicide composition which is relatively inexpensive.

DETAILED DESCRIPTION OF THE PREFERRED EMBODIMENTS

The present invention provides a composition and process for killing weeds and grasses, and, more particularly, for early (rapid) preplant burndown to prepare a field for planting, such as, for example, corn. The herbicidal composition of the present invention may be used directly to kill plants but is preferably used in the form of a liquid or solid formulation suitable for manual or mechanical application to a field. The herbicidal composition of the present invention comprises (i) ametryn [2-(ethylamino)-4-isopropylamino-6-methylthio-s-triazine], (ii) atrazine (2-cloro-4-ethylamine-6-isopropylamino-s-triazine), and (iii) paraquat (1,1-dimethyl-4,4-bipyridinium). This composition also comprises known salts of these active ingredients.

The proportion of ametryn in the composition of the present invention is 30 to 75 percent by weight active ingredient, preferably 50 to 60 percent. The proportion of atrazine is 10 to 40 percent by weight active ingredient, preferably 20 to 35 percent. The proportion of paraquat is 10 to 40 percent by weight active ingredient, preferably 17 to 20 percent. As examples of typical proportions of preferred compositions of the present invention there may be mentioned ametryn: atrazine: paraquat, ratios of about 1:0.4:0.3 and about 1:0.2:0.2. On a weight basis, the composition of the present invention contains, for example, 1.14 to 1.52 lbs. of ametryn, 0.25 to 1.0 lbs. of atrazine, and 0.25 to 0.5 lbs. of paraquat, as active ingredients applied per acre.

Compositions of the present invention include both dilute compositions, which are ready for immediate use, and concentrated compositions, which require to be diluted before use, usually with water. Preferably the compositions contain from 0.6 to 90 percent by weight of the agriculturally acceptable herbicide am&tryn. Dilute compositions ready for use preferably contain from 0.1 to 2% of the agriculturally acceptable herbicide ametryn, while concentrated compositions may contain from 20 to 90% of agriculturally acceptable herbicide ametryn although from 60 to 80% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth or gypsum or a combination thereof. They may also be in the form of dispersible powders or grains, comprising a wetting agent to facilitate the dispersion of the powder or grains in liquid. Solid compositions in the form of a powder may be applied as dusts.

Liquid compositions may comprise a solution, suspension, or dispersion of the active ingredients in water optionally containing a surface-active agent, or may comprise a solution or dispersion of the active ingredient in a water-immiscible organic solvent which is dispersed as droplets in water. The herbicidal composition is suitable either for tank mixing to produce a dilute composition ready for immediate use or for the formation of a concentrate.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzene-suphonate, sodium, calcium, and ammonium lignosulphonate, butylnaphthalene sulphonate, and a mixture of the sodium salts of diisopropyl and triisopropylnaphthalene-sulphonic acid.. Suitable non-ionic agents are the condensation products of ethylene oxide with fatty alcohols such as oleyl alcohol and cetyl alcohol, or with alkylphenols such as octyl- or nonyl- phenol or octyl-cresol. Other non-ionic agents are the partial esters derived from long chain fatty acids and hexitol anhydrides, for example sorbitan monolaurate; the condensation products of the partial ester with ethylene oxide; the lecithins; and silicone surface active agents.

The solutions or dispersions may be prepared by dissolving the active ingredients in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, xylene or trichloroethylene, or a combination thereof.

The compositions for use in the form of solutions or dispersions are generally supplied in the form of a concentrate containing a high proportion of the active ingredients, and the concentrate is then diluted with water before use.

Other additives and adjuvants may also be present in compositions of the present invention. Examples include anti-freeze agents such as ethylene glycol and propylene glycol; dyes; dispersants; rheological agents; anti-foam agents such as silicone based agents; and humectants such as ethylene glycol.

The rate of application of the composition of the present invention may depend on a number of factors, but, as a general guide, an application rate of from 0.1 to 10 lbs. per acre is suitable while from about 1 to 3.5 lbs. per acre may be preferred. Application may be 5 to 40 days before planting a crop, preferably 5 to 21 days.

The compositions of the invention may also comprise one or more additional compounds which possess biological activity.

The compositions of the present invention may be supplied in pre-mixed form or may be tank mixed shortly before application.

The invention is illustrated by the following Examples in which all parts and percentages are by weight unless otherwise indicated. Treatment rates are expressed in terms of the weight of active ingredient per acre.

EXAMPLE 1

The composition of the present invention was tested for percent burndown effectiveness, compared to pretreatment, in fields containing broadleaf weeds and grasses typically found in preplant corn fields, including Texas panicum, fall panicum, signalgrass, goosegrass, barnyardgrass, yellow & green foxtail, pigweed, wild mustard, ryegrass, vetch, volunteer wheat, Florida pusley, smartweed, and cutleaf evening primrose.

The composition of the present invention consisted of about 57% ametryn, 25% atrazine, and 18% paraquat, by weight, and was applied at a rate of about 2 lbs. per acre. On separate fields, for comparison, ametryn alone, paraquat alone, atrazine alone, and ametryn plus gramoxone were applied. The composition of the present invention was formulated by suspending 2 lbs. of the composition of the present invention per 20 gallons of water. Herbicides were rated for burndown effectiveness 6 and 8 weeks after treatment. The two resulting values were averaged. Results are shown in Table I.

TABLE I

Effectiveness of ametryn plus atrazine plus paraquat for preplant burndown.

| Herbicide(s) (lb active ingredient/acre) | Percent Burndown |
|---|---|
| ametryn (1.14) | 30 |
| paraquat (0.35) | 30 |
| paraquat (0.70) | 50 |
| atrazine (0.5) | 0 |
| ametryn (1.4) plus paraquat (0.35) | 80 |
| ametryn (1.14) plus atrazine (0.5) plus paraquat (0.35) | 92+ |

The composition of the present invention was more effective in producing burndown than that provided by the individual herbicides comprising the present composition. The present composition was more effective than the sum of the effects produced by the individual herbicides (30%+30%+0%=60%), or the sum of the effects of atrazine and ametryn plus paraquat (80%+0%=80%). This synergistic or supra-additive result was surprising and unexpected because ametryn, although used for many years to control weeds, has not been considered useful for burndown treatment, and the level of atrazine used by itself had no effect. The results were further surprising in view of the fact that the known 90–95% effectiveness of atrazine plus paraquat in burndown requires 1.6 to 2 lbs. active ingredient per acre of atrazine and 0.5 to 1.0 lbs active ingredient per acre of paraquat. These latter ingredients are applied at substantially lesser amounts in the composition of the present invention, compared to what is known in the art to be required for the use of atrazine plus paraquat for effective burndown. Also, atrazine plus paraquat will control vetch only 75–85%, but the composition of the present invention eliminates vetch and ryegrass 90–100%.

EXAMPLE 2

Rye grass and vetch often present the most difficult challenge for effective burndown treatment. The composition of the present invention was tested against rye grass and vetch in comparison with other formulations used for burndown of these plants. The composition of the present invention consisted of about 75% ametryn, 14% atrazine, and 14% paraquat, by weight, and was applied at a rate of about 2 lbs. per acre. On separate fields, for comparison, glyphosate plus ammonium sulfate or clethodium plus atrazine plus ammonium sulfate were applied. The composition of the present invention was formulated as described in Example 1. Herbicides were rated for control of rye grass and vetch, expressed as present reduction in growth compared to pretreatment growth, nine days after treatment. Results are shown in Table II.

TABLE II

Effectiveness of ametryn plus atrazine plus paraquat for control of rye grass and vetch in preplant burndown.

| Herbicide(s) (lb active ingredient/acre) | Rye Grass Control (%) | Vetch Control (%) |
| --- | --- | --- |
| Glyphosate 1.14 plus ammonium sulfate 2.55 | 84 | 68 |
| Clethodim 0.125 plus atrazine 0.5 plus ammonium sulfate 2.55 | 9 | 19 |
| Ametryn 1.5 plus paraquat 0.3 plus atrazine 0.3 | 90 | 99 |

The composition of the present invention was more effective in controlling rye and vetch than the other two standard treatments. These results were surprising and unexpected because ametryn is not useful against grasses, and atrazine and paraquat were used at levels much lower than those required for control of grasses. Atrazine plus paraquat is known to be 85–95% effective against rye grass and 75–88% against vetch if administered at 1.6 to 2.0 lbs. active ingredient/acre for atrazine and 0.5 to 1.0 lbs. active ingredient/acre for paraquat. Ametryn combined with atrazine plus paraquat produced complete control of vetch and allowed for the highly effective control of rye grass with substantially lower amounts of atrazine and paraquat, compared to what is required for the use of atrazine and paraquat alone.

In the present composition, atrazine can be used at 68 to 75% less and paraquat at 30 to 65% less than the amounts needed for the combination of atrazine plus paraquat alone presently used for burndown, and this innovation has significant human safety and environmental quality implications. As noted above, paraquat is a restricted-use herbicide that is highly toxic to humans, and atrazine is also a restricted-use herbicide that contaminates ground water and drinking water. Because the composition of the present invention uses substantially lesser amounts of atrazine and paraquat, the present composition is substantially safer than presently used formulations of atrazine plus paraquat, while being more effective in burndown treatment, including rye grass and vetch, than atrazine plus paraquat alone.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, other herbicides may be added to the present composition. It will be understood that various changes in the details, materials, and arrangements of the parts which have been described and illustrated above in order to explain the nature of this invention may be made by those skilled in the art without departing from the principle and scope of the invention as recited in the following claims.

I claim:

1. A herbicide composition for preplant burndown treatment of rye grass and vetch, consisting essentially of ametryn, paraquat, and atrazine in the proportions, by weight, of ametryn 30 to 75 percent, of atrazine 10 to 50 percent, and of paraquat 10 to 40 percent, applied with less than 0.5 lbs/acre of paraquat and less than 1.6 lbs/acre of atrazine.

2. The composition of claim 1 further comprising the salts of ametryn, paraquat, and atrazine.

3. The composition of claim 1 wherein ametryn, paraquat, and atrazine are formulated in a diluent, with the percent by weight of ametryn in the diluent ranging from 0.1 to 80 percent.

4. The composition of claim 3 wherein the diluent is water.

5. The composition of claim 4 wherein the diluent contains a surface active agent.

6. The composition of claim 3 wherein the diluent is a water-immiscible organic solvent dispersed in water.

7. The composition of claim 6 wherein said organic solvent is ethylene dichloride, isopropyl alcohol, propylene glycol, diacetone alcohol, toluene, kerosene, methylnaphthalene, xylene, or trichloroethylene, or a combination thereof.

8. The composition of claim 3 wherein the diluent is a solid.

9. The composition of claim 8 wherein the diluent is kaolin, bentonite, kieselguhr, dolomite, calcium carbonate, talc, powered magnesia, Fuller's earth, or gypsum, or a combination thereof.

10. The composition of claim 3 wherein the diluent contains ethylene glycol, propylene glycol, dispersants, wetting agents, or ethylene, or a combination thereof.

11. A method for preplant burndown treatment of rye grass and vetch, comprising:

a. formulating a composition consisting essentially of ametryn, atrazine and paraquat in the proportions, by weight, of ametryn 30 to 75 percent, of atrazine 10 to 50 percent, and of paraquat 10 to 40 percent;

b. mixing said composition in a diluent; and c. applying said composition in said diluent to a field at a rate of 0.1 to 8 lbs per acre, 5 to 40 days before planting a crop, applying less than 0.5 lbs/acre of paraquat and less than 1.6 lbs/acre of atrazine.

12. The method of claim 11 wherein the percentage by weight of ametryn in said diluent ranges from 0.1 to 80 percent.

13. The method of claim 11 wherein said diluent is water.

14. The method of claim 13 wherein the diluent contains a surface active agent.

15. The method of claim 11 wherein the diluent is a water-immiscible organic solvent dispersed in water.

16. The method of claim 15 wherein said organic solvent is ethylene dichloride, isopropyl alcohol, propylene glycol, diacetone alcohol, toluene, kerosene, methylnaphthalene, xylene, or trichloroethylene, or a combination thereof.

17. The method of claim 11 wherein said diluent is a solid.

18. The method of claim 17 wherein the diluent is kaolin, bentonite, kieselguhr, dolomite, calcium carbonate, talc, powered magnesia, Fuller's earth, or gypsum, or a combination thereof.

19. The method of claim 12 wherein the diluent contains ethylene glycol, propylene glycol, dispersants, wetting agents, or ethylene, or a combination thereof.

* * * * *